United States Patent
Kurian

(12)
(10) Patent No.: US 6,350,895 B1
(45) Date of Patent: Feb. 26, 2002

(54) TRANSESTERIFICATION PROCESS USING YTTRIUM AND SAMARIUM COMPOUND CATALYSTIS

(75) Inventor: Joseph Varapadavil Kurian, Newark, DE (US)

(73) Assignee: E. I. Du Pont de Nemours and Company, Wilmington, DE (US)

( * ) Notice: Subject to any disclaimer, the term of this patent is extended or adjusted under 35 U.S.C. 154(b) by 0 days.

(21) Appl. No.: 09/505,789

(22) Filed: Feb. 17, 2000

Related U.S. Application Data

(60) Provisional application No. 60/126,557, filed on Mar. 26, 1999.

(51) Int. Cl.[7] ................................................. C07C 67/02
(52) U.S. Cl. ............................................................... 560/92
(58) Field of Search .................................. 560/99, 98, 76, 560/92

(56) References Cited

U.S. PATENT DOCUMENTS

| | | | |
|---|---|---|---|
| 2,727,882 A | 12/1955 | Vodonik | |
| 2,820,023 A | 1/1958 | Cavanaugh et al. | |
| 2,829,153 A | 4/1958 | Vodonik | 260/470 |
| 2,932,625 A | 4/1960 | Burton et al. | 260/75 |
| 2,933,476 A | 4/1960 | Fisher | 260/75 |
| 2,973,341 A | 2/1961 | Hippe et al. | 260/75 |
| 3,054,776 A | 9/1962 | Higgins | 260/75 |
| 3,167,531 A | 1/1965 | Parker et al. | 260/75 |
| 3,192,184 A | 6/1965 | Brill | 260/75 |
| 3,438,942 A | 4/1969 | Scheller et al. | 260/75 |
| 3,506,622 A | 4/1970 | Higgins | 260/75 |
| 3,523,104 A | 8/1970 | Dobinson | 260/75 |
| 3,532,671 A | 10/1970 | Carlson et al. | 260/75 |
| 3,609,125 A | 9/1971 | Fujimoto et al. | 260/75 |
| 3,671,379 A | 6/1972 | Evans et al. | 161/173 |
| 3,676,485 A | 7/1972 | Lewis et al. | 260/45.75 |
| 3,706,711 A | 12/1972 | Conix et al. | 260/75 |
| 3,936,421 A | 2/1976 | Hayashi et al. | 260/75 |
| 4,049,635 A | 9/1977 | Cleary | 260/75 |
| 4,056,514 A | 11/1977 | Strehler et al. | 260/75 |
| 4,096,122 A | 6/1978 | Schade et al. | 260/75 |
| 4,110,316 A | 8/1978 | Edging et al. | 526/68 |
| 4,289,895 A | 9/1981 | Burkhardt et al. | 560/92 |
| 5,208,297 A | 5/1993 | Ford et al. | 525/415 |
| 5,235,031 A | 8/1993 | Drysdale et al. | 528/354 |
| 5,292,859 A | 3/1994 | Ford et al. | 528/354 |
| 5,340,909 A | 8/1994 | Doerr et al. | 528/276 |
| 5,434,239 A | 7/1995 | Bhatia | 528/274 |
| 5,459,229 A | 10/1995 | Kelsey et al. | 528/275 |
| 5,510,454 A | 4/1996 | Stouffer et al. | 528/308.1 |
| 5,540,868 A | 7/1996 | Stouffer et al. | 264/13 |
| 5,559,205 A | 9/1996 | Hansen et al. | 528/279 |
| 5,633,018 A | 5/1997 | Stouffer et al. | 425/8 |
| 5,654,380 A | 8/1997 | Kawai et al. | 525/439 |
| 5,663,281 A | 9/1997 | Brugel | 528/272 |
| 5,670,606 A | 9/1997 | Stouffer et al. | 528/272 |
| 5,677,415 A | 10/1997 | Bhatia | 528/176 |
| 5,693,808 A | 12/1997 | Langhals | 546/37 |
| 5,703,179 A | 12/1997 | Asakura et al. | 526/59 |
| 5,763,104 A | 6/1998 | Stouffer et al. | 528/503 |
| 5,786,443 A | 7/1998 | Lowe | 528/272 |
| 5,798,433 A | 8/1998 | Schmidt et al. | 528/279 |
| 5,811,496 A | 9/1998 | Iwasyk et al. | 252/444 |
| 5,840,957 A | 11/1998 | Kurian et al. | 560/92 |
| 5,891,985 A | 4/1999 | Brugel | 528/283 |
| 5,990,265 A | 11/1999 | Blanchard et al. | 528/298 |

FOREIGN PATENT DOCUMENTS

| | | | |
|---|---|---|---|
| DE | 42 21 969 A1 | 7/1992 | C08L/77/00 |
| JP | 39-24039 | 4/1964 | |
| JP | WO00/96301 | 5/2000 | |
| SU | 664427 | 1/1977 | |
| WO | 99/11845 | 3/1999 | |
| WO | 99/54040 | 10/1999 | |

OTHER PUBLICATIONS

Traub et al, Mechanical Properties of Fibers Made of Polytrimethylene Terephthalate, *Chemical Fibers*, 45, 110–111, Apr. 1995.

Schaufoff et al., New Developments in the Production of Polytrimethylene Terephthalate (PTT), *Man–Made Fiber Year Book*, 1996.

U.S. Patent Application 09/503,599, Filed Feb. 11, 2000, Griffith et al.

*Primary Examiner*—Gary Geist
*Assistant Examiner*—Robert W. Deemie
(74) *Attorney, Agent, or Firm*—Barbara C. Siegell; Nancy S. Mayer; Mark D. Kuller

(57) ABSTRACT

This invention relates to an improvement for the preparation of bis(3-hydroxypropyl) dicarboxylate monomers using 1,3-propanediol and a dialkyl dicarboxylate in the presence of a catalytic amount of such yttrium and/or samarium compounds as yttrium/samarium acetylacetonate or tris(2,2,6,6-tetramethyl-3,5-heptanedionato) yttrium/samarium which act as a catalyst for the transesterification reaction

5 Claims, 2 Drawing Sheets

TRANSESTERIFICATION PROCESS USING YTTRIUM AND SAMARIUM COMPOUND CATALYSTIS

CROSS REFERENCE TO RELATED APPLICATION

This application claims the priority benefit of provisional application No. 06/126,557, filed Mar. 26, 1999.

FIELD OF THE INVENTION

This invention relates to processes for making bis(3-hydroxypropyl) dicarboxylate monomer such as bis(3-hydroxypropyl) terephthalate and bis(3-hydroxypropyl) naphthalenedicarboxylate monomers from $C_1$–$C_4$ dialkyl esters of terephthalic acid or naphthalene dicarboxylic acid and 1,3-propanediol in the presence of a yttrium or samarium compound transesterification catalyst.

TECHNICAL BACKGROUND

Preparation of polyester resins by transesterification of a $C_1$–$C_4$ dialkyl ester of terephthalic acid and a diol or of a $C_1$–$C_4$ dialkyl ester of naphthalene dicarboxylic acid acid and a diol, followed by polycondensation is well known in the art.

Generally, the $C_1$–$C_4$ dialkyl ester of terephthalic acid or naphthalene dicarboxylic acid and the diol are reacted in the presence of a transesterification catalyst at elevated temperature and atmospheric pressure to form a monomer and a $C_1$–$C_4$ alkanol corresponding to the $C_1$–$C_4$ alkanol components of the dialkyl ester. The $C_1$–$C_4$ alkanol is removed as it is formed during the reaction. Oligomers having a degree of polymerization of about 4 or less can also be formed. The monomer and any oligomer can then be polymerized at higher temperatures under reduced pressure in the presence of a polycondensation catalyst to form the desired polyester resin. These reactions can be carried out in batch or continuous processes.

Transesterification catalysts known in the art include titanium, manganese, lanthanum and zinc compounds. For example, U.S. Pat. No. 3,671,379 to Evans et al., discloses a process for producing poly(trimethylene terephthalate) using a titanium catalyst compound in both the transesterification and the polycondensation reactions. Cerium and lead acetylacetonate catalysts for the transesterification of dimethyl terephthalate with ethylene glycol are disclosed by Carlson et al. in U.S. Pat. No. 3,532,671. Lanthanum compounds, such as lanthanum acetate, are disclosed by Cavanaugh et al in U.S. Pat. No. 2,820,023 to be effective transestrification catalysts for the preparation of bis(2-hydroxyethyl) terephthalate from dimethyl terephthalate (DMT) and ethylene glycol.

New process improvements which increase transesterification rates resulting in increased throughput and reduced cost of production of bis(3-hydroxypropyl) carboxylate monomer such as bis(3-hydroxypropyl) terephthalate monomer and bis(3-hydroxypropyl) naphthalene dicarboxylate monomer are of significant interest to the chemical industry.

SUMMARY OF THE INVENTION

The present invention is an improved process for making bis(3-hydroxypropyl) dicarboxylate monomer, comprising contacting a $C_1$–$C_4$ dialkyl ester of dicarboxcylic acid with 1,3-propanediol in the presence of a catalytic amount of at least one transesterification catalyst selected from the group consisting of compounds of yttrium and samarium at a temperature from about 150° C. to about 245° C.

DETAILED DESCRIPTION OF THE INVENTION

Figure 1:
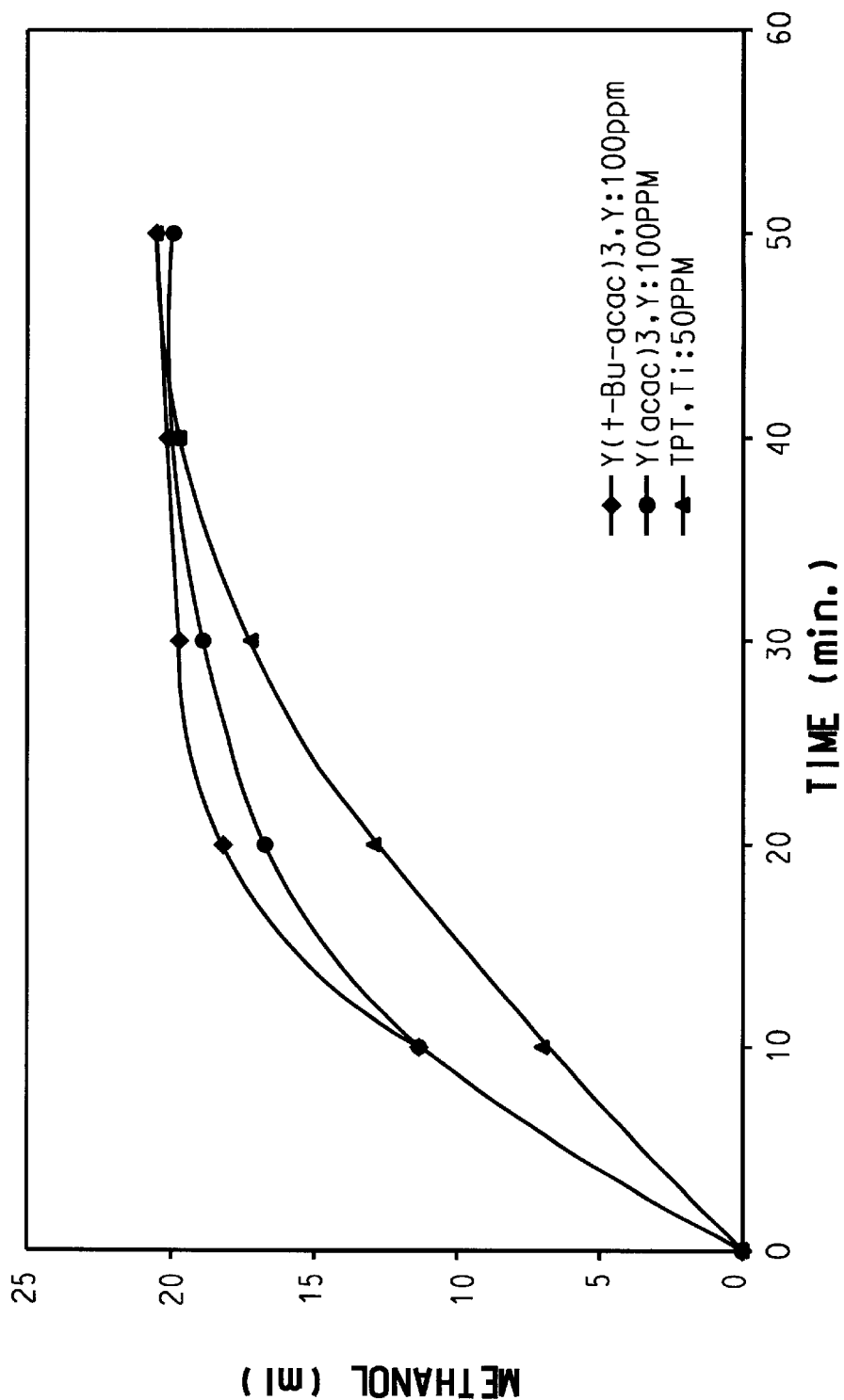
FIG. 1 is a plot depicting the amount of methanol collected versus time for Example 1 and Example 2 illustrating the invention and Comparative Example A.

This invention is a transesterification process for making bis(3-hydroxypropyl) dicarboxylate monomer such as bis(3-hydroxypropyl) terephthalate monomer and bis(3-hydroxypropyl) naphthalenedicarboxylate monomer. A $C_1$–$C_4$ dialkyl ester of the corresponding dicarboxylic acid is contacted or combined with 1,3-propanediol in the presence of a yttrium or samarium compound transesterification catalyst. Preferably such catalyst is selected from the group consisting of a yttrium or samarium beta-diketonate, a yttrium or samarium beta-ketoester, a yttrium or samarium beta-diester and mixtures thereof. The process is conducted at a temperature from about 150° C. to about 245° C., preferably with a mole ratio of 1,3-propanediol to the dialkyl ester of about 1.1:1 to about 2.2:1.

The $C_1$–$C_4$ dialkyl esters of dicarboxylic acids which are suitable as reactants in the process of the current invention include dimethyl terephthalate, diethyl terephthalate, di-n-propyl terephthalate, di-isoproyl terephthalate, di-n-butyl terephthalate, di-isobutyl terephthalate, di-t-butyl terephthalate, dimethyl-2,6-naphthalene dicarboxylate, diethyl-2,6-naphthalene dicarboxylate, di-n-propyl-2,6-naphthalene dicarboxylate, di-isopropyl-2,6-naphthalene dicarboxylate, di-n-butyl naphthalene dicarboxylate, di-isobutyl naphthalene dicarboxylate and di-t-butyl naphthalene dicarboxylate. These $C_1$–$C_4$ dialkyl esters of the dicarboxylic acid are diesters that are the reaction product of the dicarboxylic acid and an alkanol containing 1–4 carbons. Preferably, the dialkyl ester is dimethyl terephthalate (DMT) or dimethyl-2,6-naphthalene dicarboxylate (DMN).

Minor amounts of one or more other diols (other than 1,3-propanediol), such as in an amount less than about 10 mole percent based on the total diol (including the 1,3-propanediol and the other diols), and/or minor amounts of one or more other $C_1$–$C_4$ dialkyl esters of a dicarboxylic acid (other than terephthalic acid or naphthalene dicarboxylic acid), such as in an amount less than about 10 mole percent based on the total $C_1$–$C_4$ dialkyl ester of dicarboxylic acid (including the $C_1$–$C_4$ dialkyl ester of dicarboxylic acid and the other $C_1$–$C_4$ dialkyl esters of dicarboxylic acid), can be added before or during the transesterification reaction, followed by a polycondensation reaction to form copolymers. For instance, the diol (other than 1,3-propanediol) can be ethylene glycol, 1,4-butanediol, or mixtures thereof. The dicarboxylic acid or diacid (other than terephthalic acid or naphthalene dicarboxylic acid) can be isophthalic acid, adipic acid, or mixtures thereof. The other diols and dicarboxcylic acids and the amounts thereof, if used, are used in amounts which do not interfere with the transesterification reaction, and if such other diols or dicarboxcylic acids are used, the transesterification result is simply a mixture of the bis dicarboxylate monomers.

The yttrium (Y) compounds useful as transesterification catalysts in the present invention include yttrium beta-diketonate compounds, yttrium beta-ketoester compounds, such as yttrium tris(methylacetoacetate), yttrium beta-diester compounds, such as yttrium tris(dialkylmalonate), and mixtures thereof. The yttrium beta-diketonate compounds useful as transesterification catalysts in the present invention include yttrium tris(acetylacetonate) (also known as Y(acac)3) and yttrium tris(2,2,6,6-tetramethyl-3,5-heptanedionate) (also known as yttrium t-butylacetylacetonate or Y(t-Bu-acac)3). Other yttrium beta-diketonate compounds useful as transesterification catalysts in the present invention include tris(t-butylhydroxymethylene-d,l-camphorato) yttrium, yttrium tris(2,2,6-trimethyloctan-3,5-dionate), yttrium tris (hexafluoroacetylacetonate). The preferred yttrium beta-diketonate compounds are yttrium tris(acetylacetonate) and yttrium tris(2,2,6,6-tetramethyl-3,5-heptanedionate).

The samarium (Sm) compounds useful as transesterification catalysts in the present invention include samarium beta-diketonate compounds, samarium beta-ketoester compounds, such as samarium tris(methylacetoacetate), samarium beta-diester compounds, such as samarium tris (dialkylmalonate), and mixtures thereof. The samarium beta-diketonate compounds useful as transesterification catalysts in the present invention include samarium tris (acetylacetonate) (also known as Sm(acac)3) and samarium tris(2,2,6,6-tetramethyl-3,5-heptanedionate) (also known as samarium t-butylacetylacetonate or Sm(t-Bu-acac)3). Other samarium beta-diketonate compounds useful as transesterification catalysts in the present invention include tris(t-butylhydroxymethylene-d,l-camphorato) samarium, samarium tris(2,2,6-trimethyloctan-3,5-dionate), samarium tris(hexafluoroacetylacetonate). The preferred samarium beta-diketonate compounds are samarium tris (acetylacetonate) and samarium tris(2,2,6,6-tetramethyl-3,5-heptanedionate).

The yttrium and samarium compound catalysts are added to the transesterification reaction in concentrations sufficient to cause catalytic activity such as in concentrations corresponding to about 10 ppm to about 550 ppm, preferably to about 35 ppm to about 320 ppm of elemental yttrium or samarium based on $C_1$–$C_4$ dialkyl ester added to the reaction. The term "ppm" is used herein to mean parts per million and is equal to micrograms per gram. When dimethyl terephthalate is the dialkyl ester used in the reaction, the yttrium and samarium compound catalysts are preferably added in concentrations corresponding to about 50 ppm to about 300 ppm of elemental yttrium or samarium based on dimethyl terephthalate. The catalyst can be added directly to the contacted or combined reactants, or added as a solution in 1,3-propanediol.

The transesterification process of the current invention can be conducted by reacting the $C_1$–$C_4$ dialkyl ester of the dicarboxylic acid with the 1,3-propanediol in the presence of the yttrium or samarium compound catalysts at about atmospheric pressure and at a temperature from about 155° C. to about 245° C., preferably about 180° C. to about 240° C. with a mole ratio of 1,3-propanediol to the $C_1$–$C_4$ dialkyl ester of about 1.1:1 to about 2.2:1, preferably about 1.4:1 to about 2.0:1. Residence times of reactants and resulting product in a reaction vessel in which the transesterification reaction occurs are generally from about 0.5 hours to about 4 hours.

Preferably, the reaction vessel is purged with an inert gas, such as nitrogen, before heating. Further, the liquid mixture in the reaction vessel can be stirred. The process can be performed in batch or continuous process.

In the transesterification process, the $C_1$–$C_4$ dialkyl ester of the carboxylic acid reacts with 1,3-propanediol to form the bis(3-hydroxypropyl) ester derivative of the dicarboxylic acid. Depending on the relative concentration of reactants and process conditions, the reaction can also produce oligomers having a degree of polymerization of about 4 or less.

The $C_1$–$C_4$ dialkyl esters of dicarboxylic acids suitable for use in this invention react with 1,3-propanediol to form bis(3-hydroxypropyl) esters and a monohydric alcohol. The monohydric alcohol is a $C_1$–$C_4$ alkanol corresponding to the $C_1$–$C_4$ alkanol components of the dialkyl ester. Thus, the monohydric alcohol, or the $C_1$–$C_4$ alkanol, is methanol, ethanol, propanol, or butanol. For example, 1,3-propanediol is reacted with dimethyl terephthalate in the presence of a yttrium or samarium compound transesterificatin catalyst to form bis(3-hydroxypropyl) terephthalate and methanol.

Other typically undesired byproducts can be formed including allyl alcohol, acrolein and acrylic acid which can be minimized or eliminated by a proper selection of the relative concentration of reactants and process conditions.

The $C_1$–$C_4$ alkanol can be removed by distillation as it is formed during the reaction. This separates bis(3-hydroxypropyl) terephthalate or bis(3-hydroxypropyl) naphthalene dicarboxylate and any oligomers thereof from a product of the reaction. The bis(3-hydroxypropyl) monomer can be polymerized to form poly(trimethylene terephthalate) or poly(trimethylene naphthalate) which have a number of end uses including but not limited to carpeting, hosiery, fishing line, films, and paper making press fabrics.

High quality poly(trimethylene terephthalate) or poly (trimethylene naphthalate) can be made from bis(3-hydroxypropyl) dicarboxylate monomers and oligomers thereof using polycondensation methods known in the art. For example, after transesterification, the temperature can be raised to be in the range of about 240° C. to about 290° C. and the pressure can be reduced to below about 1 mm of mercury absolute pressure in the presence of a suitable catalyst, such as titanium or antimony compounds, to polymerize the monomer and oligomers thereof with removal of excess 1,3-propanediol.

As illustrated in Examples 1–3 versus Comparative Example A, yttrium and samarium beta-diketonate compounds, such as yttrium tris(acetylacetonate) and samarium tris(acetylacetonate), have been found to provide faster transesterification rates than Tyzor® TPT (organic titanate) available from E. I. du Pont de Nemours and Company, Wilmington, Del., for the reaction of 1,3-propanediol with dimethyl terephthalate. Improved rates increases throughput and reduce the cost of production of poly(trimethylene terephthalate) monomer. Alternatively, less catalyst (mole basis) can be used compared to Tyzor® TPT.

EXAMPLES

Example 1

Transesterification Reaction of Dimethyl Terephthalate Using a 1,3-propanediol Using Yttrium Tris (acetylacetonate) Catalyst This example demonstrated the transesterification reaction of dimethyl terephthalate with 1,3-propanediol using yttrium tris(acetylacetonate) as the transesterification catalyst (100 ppm Y based on final polymer) to form bis(3-hydroxypropyl) terephthalate.

A 250 ml flask equipped with a stirrer and distillation column was charged with 58.5 g of dimethyl terephthalate (DMT) and 41 g of 1,3-propanediol (purchased from Degussa AG, with offices in Wolfgang, Germany) for a mole ratio of 1,3-propanediol:DMT of 1.8:1. The flask was then purged with nitrogen and the contents of the flask were heated. When the temperature inside the flask reached about 150° C. and all of the DMT had melted, the stirrer was started. When the temperature reached 210° C., 27 mg of yttrium tris(acetylacetonate) (purchased from Aldrich Chemical Co., Milwaukee, Wis.) (100 ppm of yttrium based on final polymer, 106 ppm based on DMT) was added. Upon addition of yttrium tris(acetylacetonate), methanol was evolved. The methanol was removed as a liquid condensate by distillation. The temperature was held at 210° C. and the amount of liquid methanol collected was measured every ten minutes until no more methanol was evolved. The cumulative amount of methanol collected versus time is shown in Table 1 and FIG. 1. A total of 20 ml of methanol was collected in 50 minutes. The theoretical amount of methanol for complete transesterification is 24.4 ml. Some methanol may have been flushed away with the nitrogen purge and small amounts may have remained in the reaction mixture and been removed upon application of vacuum during polycondensation. As illustrated in FIG. 1, the transesterification rate for Yttrium tris(acetylacetonate) catalyst (Y(acac)3) in this Example 1 was faster than that of Tyzor® TPT catalyst used in Comparative Example A.

Example 2
Transesterification Reaction of Dimethyl Terephthalate with 1,3-propanediol Using a Yttrium T-butylacetylacetonate Catalyst This example demonstrated the transesterification reaction of dimethyl terephthalate with 1,3-propanediol using yttrium t-butylacetylacetonate as the transesterification catalyst (100 ppm Y based on final polymer) to form bis(3-hydroxypropyl) terephthalate.

The procedure of Example 1 was followed except that 44.6 mg of yttrium t-butylacetylacetonate (purchased from Strem Chemical Inc., Newburyport, Mass.) (100 ppm of yttrium based on final polymer, 106 ppm based on DMT) was used as the transesterification catalyst. The amount of methanol collected vs. time is shown in Table 1 and FIG. 1. A total of 20.5 ml of methanol was collected in 50 minutes. The theoretical amount of methanol for complete transesterification is 24.4 ml. As illustrated in FIG. 1, the transesterification rate for yttrium t-butylacetylacetonate catalyst (Y(t-butyl-acac)3) in this Example 2 was faster than that of Tyzor® TPT catalyst used in Comparative Example A.

TABLE 1

Methanol Evolution vs. Time Using Ti (50 ppm)/Y (100 ppm) Catalysts

| Time (min) | Comparative Example A Tyzor ® TPT MeOH (ml) | Example 1 Y(acac)3 MeOH (ml) | Example 2 Y(t-Bu-acac)3 MeOH (ml) |
| --- | --- | --- | --- |
| 0 | 0 | 0 | 0 |
| 10 | 7 | 11.5 | 11.5 |
| 20 | 13 | 16.5 | 18 |
| 30 | 17 | 18.5 | 19.5 |
| 40 | 19.5 | 19.5 | 20 |
| 50 | 20.5 | 20 | 20.5 |

Example 3
Transesterification Reaction of Dimethyl Terephthalate Using a 1,3-propanediol Using a Samarium Acetylacetonate Catalyst This example demonstrated the transesterification reaction of dimethyl terephthalate with 1,3-propanediol using samarium acetylacetonate as the transesterification catalyst (160 ppm Sm based on final polymer) to form bis(3-hydroxypropyl) terephthalate.

Figure 2:
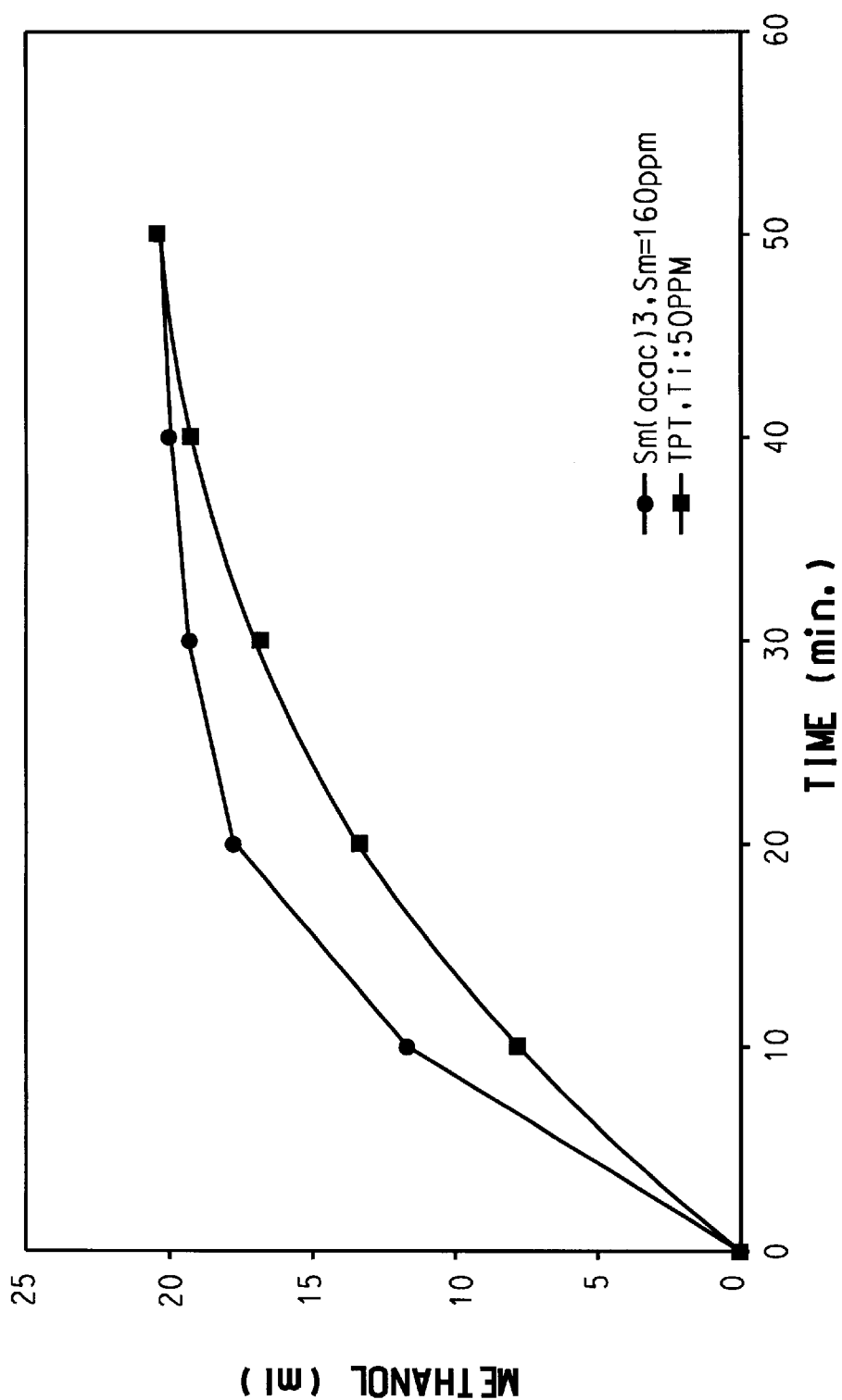
FIG. 2 is a plot showing the amount of methanol collected versus time for Example 3 illustrating the invention and Comparative Example A.

The procedure of Example 1 was followed except that 29.6 mg of samarium acetylacetonate (purchased from Strem Chemical Inc., Newburyport, Mass.) (160 ppm of samarium based on final polymer, 170 ppm based on DMT) was used as the transesterification catalyst. The amount of methanol collected vs. time is shown in Table 2 and FIG. 2. A total of 20.5 ml of methanol was collected in 50 minutes. The theoretical amount of methanol for complete transesterification is 24.4 ml. As illustrated in FIG. 2, the transesterification rate for samarium acetylacetonate catalyst (Sm (acac)3) in this Example 3 was faster than that of Tyzor® TPT catalyst used in Comparative Example A.

TABLE 2

Methanol Evolution vs. Time Using Ti (50 ppm)/Sm (160 ppm) Catalysts

| Time (min) | Comparative Example A Tyzor ® TPT MeOH (ml) | Example 3 Sm(acac)3 MeOH (ml) |
| --- | --- | --- |
| 0 | 0 | 0 |
| 10 | 7 | 11.5 |
| 20 | 13 | 17.5 |
| 30 | 17 | 19.5 |
| 40 | 19.5 | 20.2 |
| 50 | 20.5 | 20.5 |

Comparative Example A

This example demonstrated the transesterification reaction of dimethyl terephthalate with 1,3-propanediol using Tyzor® TPT as the transesterification catalyst (50 ppm Ti based on final polymer) to form bis(3-hydroxypropyl) terephthalate.

The procedure of Example 1 was followed except that 18.4 mg of Tyzor® TPT (E. I. du Pont de Nemours and Company, of Wilmington, Del.) (50 ppm of Ti based on final polymer, 53 ppm based on DMT) was used as the transesterification catalyst. The amount of methanol collected vs. time is shown in Table 1 and FIG. 1. A total of 20.5 ml of methanol was collected in 50 minutes. The theoretical amount of methanol for complete transesterification is 24.4 ml.

What is claimed is:

1. A process for making bis(3-hydroxypropyl) dicarboxylate monomers, comprising contacting a $C_1$–$C_4$ dialkyl ester of a dicarboxylic acid with 1,3-propanediol in the presence of a catalytic amount of at least one transesterfication catalyst selected from the group consisting compounds of yttrium and samarium at a temperature from about 150° C. to about 245° C.

2. The process of claim 1 wherein the dicarboxylic acid is terephthalic acid.

3. The process of claim 1 wherein the dicarboxylic acid is 2,6-naphthalenedicarboxylic acid.

4. The process of claim 1 where the yttrium compound transesterification catalyst is selected from the group consisting of a yttrium beta-diketonate, a yttrium beta-ketoester, a yttrium beta-diester and mixtures thereof.

5. The process of claim 1 wherein the mole ratio of 1,3-propanediol to the dialkyl ester is about 1.1:1 to about 2.2:1.

* * * * *

UNITED STATES PATENT AND TRADEMARK OFFICE
CERTIFICATE OF CORRECTION

PATENT NO. : 6,350,895 B1
DATED : February 26, 2002
INVENTOR(S) : Joseph Varapadavil Kurian It is certified that error appears in the above-identified patent and that said Letters Patent is hereby corrected as shown below:

<u>Title page, Item [54] and Column 1, line 3,</u>
Replace "CATALYSTIS" with -- CATALYSTS --

Item [57], ABSTRACT,
Line 7, replace "reaction" with -- reaction. --

<u>Column 2,</u>
Line 58, replace "boxcylic" with -- boxylic --
Line 60, replace "dicarboxcylic" with -- dicarboxylic --

<u>Column 4,</u>
Line 12, replace "transesterificaton" with -- transesterification --
Line 55, replace "Using a" with -- With --

<u>Column 5,</u>
Line 26, replace "T-butylacetylacetonate" with -- t-butylacetylacetonate --
Line 63, replace "Using a" with -- With --

Signed and Sealed this

Third Day of September, 2002

Attest:

*Attesting Officer*

JAMES E. ROGAN
*Director of the United States Patent and Trademark Office*